(12) United States Patent
Lin et al.

(10) Patent No.: US 6,559,174 B2
(45) Date of Patent: May 6, 2003

(54) N-ARYLSULFONYL ARYL AZA-BICYCLIC DERIVATIVES AS POTENT CELL ADHESION INHIBITORS

(75) Inventors: Linus S. Lin, Westfield, NJ (US); Shrenik K. Shah, Metuchen, NJ (US); Linda L. Chang, Wayne, NJ (US); William K. Hagmann, Westfield, NJ (US); Richard A. Mumford, Red Bank, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/097,028

(22) Filed: Mar. 13, 2002

(65) Prior Publication Data

US 2002/0193399 A1 Dec. 19, 2002

Related U.S. Application Data

(60) Provisional application No. 60/277,235, filed on Mar. 20, 2001.

(51) Int. Cl.[7] .......................... A61K 31/47; A61K 31/40; C07D 217/00; C07D 471/04; C07D 487/04
(52) U.S. Cl. .......................... 514/406; 514/303; 514/309; 514/338; 514/339; 514/416; 546/120; 546/141; 546/275.7; 546/277.1; 548/360.5; 548/482
(58) Field of Search ................................ 546/141, 120, 546/275.7, 277.1; 548/360.5, 482; 514/303, 309, 338, 339, 406, 416

(56) References Cited

FOREIGN PATENT DOCUMENTS

| WO | WO 98/53814 | 12/1998 |
|----|-------------|---------|
| WO | WO 99/06437 | 2/1999 |

*Primary Examiner*—Bernard Dentz
(74) *Attorney, Agent, or Firm*—Mollie M. Yang; David L. Rose

(57) ABSTRACT

Compounds of Formula I are antagonists of VLA-4 and/or alpha4/beta7, and as such are useful in the inhibition or prevention of cell adhesion and cell-adhesion mediated pathologies. These compounds may be formulated into pharmaceutical compositions and are suitable for use in the treatment of AIDS-related dementia, allergic conjunctivitis, allergic rhinitis, Alzheimer's disease, asthma, atherosclerosis, autologous bone marrow transplantation, certain types of toxic and immune-based nephritis, contact dermal hypersensitivity, inflammatory bowel disease including ulcerative colitis and Crohn's disease, inflammatory lung diseases, inflammatory sequelae of viral infections, meningitis, multiple sclerosis, multiple myeloma, myocarditis, organ transplantation, psoriasis, pulmonary fibrosis, restenosis, retinitis, rheumatoid arthritis, septic arthritis, stroke, tumor metastasis, uveititis, and type I diabetes.

14 Claims, No Drawings

N-ARYLSULFONYL ARYL AZA-BICYCLIC DERIVATIVES AS POTENT CELL ADHESION INHIBITORS

CROSS REFERENCE TO RELATED APPLICATIONS

This application is based on, and claims priority from, U.S. provisional application No. 60/277,235, filed Mar. 20, 2001, which is herby incorporated by reference in its entirety.

SUMMARY OF THE INVENTION

The compounds of the present invention are antagonists of the VLA-4 integrin ("very late antigen-4"; CD49d/CD29; or $\alpha_4\beta_1$), the $\alpha_4\beta_7$ integrin (LPAM-1 and $\alpha_4\beta_p$), and/or the $\alpha_9\beta_1$ integrin, and are useful in the treatment, prevention and suppression of diseases mediated by VLA-4-, $\alpha_4\beta_7$-, and/or $\alpha_9\beta_1$-binding and cell adhesion and activation.

BACKGROUND OF THE INVENTION

The present invention relates to potent substituted N-arylsulfonylated-proline derivatives which are useful for the inhibition and prevention of leukocyte adhesion and leukocyte adhesion-mediated pathologies. This invention also relates to compositions containing such compounds and methods of treatment using such compounds.

Many physiological processes require that cells come into close contact with other cells and/or extracellular matrix. Such adhesion events may be required for cell activation, migration, proliferation and differentiation. Cell-cell and cell-matrix interactions are mediated through several families of cell adhesion molecules (CAMs) including the selectins, integrins, cadherins and immunoglobulins. CAMs play an essential role in both normal and pathophysiological processes. Therefore, the targeting of specific and relevant CAMs in certain disease conditions without interfering with normal cellular functions is essential for an effective and safe therapeutic agent that inhibits cell—cell and cell-matrix interactions.

The integrin superfamily is made up of structurally and functionally related glycoproteins consisting of a and b heterodimeric, transmembrane receptor molecules found in various combinations on nearly every mammalian cell type. VLA-4 ("very late antigen-4"; CD49d/CD29; or $\alpha_4\beta_1$) is an integrin expressed on all leukocytes, except platelets and mature neutrophils, including dendritic cells and macrophage-like cells and is a key mediator of the cell—cell and cell-matrix interactions of these cell types. The ligands for VLA-4 include vascular cell adhesion molecule-1 (VCAM-1) and the CS-1 domain of fibronectin (FN). VCAM-1 is a member of the Ig superfamily and is expressed in vivo on endothelial cells at sites of inflammation. VCAM-1 is produced by vascular endothelial cells in response to pro-inflammatory cytokines. The CS-1 domain is a 25 amino acid sequence that arises by alternative splicing within a region of fibronectin. A role for VLA-4/CS-1 interactions in inflammatory conditions has been proposed (see M. J. Elices, "The integrin $\alpha_4\beta_1$ (VLA-4) as a therapeutic target" in *Cell Adhesion and Human Disease*, Ciba Found. Symp., John Wiley & Sons, NY, 1995, p. 79).

$\alpha_4\beta_7$ (also referred to as LPAM-1 and $\alpha_4\beta_p$) is an integrin expressed on leukocytes and is a key mediator of leukocyte trafficking and homing in the gastrointestinal tract. The ligands for $\alpha_4\beta_7$ include mucosal addressing cell adhesion molecule-1 (MadCAM-1) and, upon activation of $\alpha_4\beta_7$, VCAM-1 and fibronectin (Fn). MadCAM-1 is a member of the Ig superfamily and is expressed in vivo on endothelial cells of gut-associated mucosal tissues of the small and large intestine ("Peyer's Patches") and lactating mammary glands. MadCAM-1 can be induced in vitro by proinflammatory stimuli. MadCAM-1 is selectively expressed at sites of lymphocyte extravasation and specifically binds to the integrin, $\alpha_4\beta_7$.

The $\alpha_9\beta_1$ integrin is found on airway smooth muscle cells, non-intestinal epithelial cells, and neutrophils, and, less so, on hepatocytes and basal keratinocytes. Neutrophils, in particular, are intimately involved in acute inflammatory responses. Attenuation of neutrophil involvement and/or activation would have the effect of lessening the inflammation. Thus, inhibition of $\alpha_9\beta_1$ binding to its respective ligands would be expected to have a positive effect in the treatment of acute inflammatory conditions.

Neutralizing anti-$\alpha_4$ antibodies or blocking peptides that inhibit the interaction between VLA-4 and/or $\alpha_4\beta_7$ and their ligands have been shown efficacious both prophylactically and therapeutically in several animal models of disease, including i) experimental allergic encephalomyelitis, a model of neuronal demyelination resembling multiple sclerosis; ii) bronchial hyperresponsiveness in sheep and guinea pigs as models for the various phases of asthma; iii) adjuvant-induced arthritis in rats as a model of inflammatory arthritis; iv) adoptive autoimmune diabetes in the NOD mouse; v) cardiac allograft survival in mice as a model of organ transplantation; vi) spontaneous chronic colitis in cotton-top tamarins which resembles human ulcerative colitis, a form of inflammatory bowel disease; vii) contact hypersensitivity models as a model for skin allergic reactions; viii) acute nephrotoxic nephritis; ix) tumor metastasis; x) experimental autoimmune thyroiditis; xi) ischemic tissue damage following arterial occlusion in rats; and xii) inhibition of TH2 T-cell cytokine production including IL-4 and IL-5 by VLA-4 antibodies which would attenuate allergic responses (J. Clinical Investigation 100, 3083 (1997). The primary mechanism of action of such antibodies appears to be the inhibition of lymphocyte and monocyte interactions with CAMs associated with components of the extracellular matrix, thereby limiting leukocyte migration to extravascular sites of injury or inflammation and/or limiting the priming and/or activation of leukocytes. Animal models of these diseases may also be used to demonstrate efficacy of small molecule VLA-4 antagonists.

There is additional evidence supporting a possible role for VLA-4 interactions in other diseases, including rheumatoid arthritis; various melanomas, carcinomas, and sarcomas, including multiple myeloma; inflammatory lung disorders; acute respiratory distress syndrome (ARDS); pulmonary fibrosis; atherosclerotic plaque formation; restenosis; uveitis; and circulatory shock (for examples, see A. A. Postigo et al., "The $\alpha_4\beta_1$/VCAM-1 adhesion pathway in physiology and disease.", *Res. Immunol.*, 144, 723 (1994) and J. -X. Gao and A. C. Issekutz, "Expression of VCAM-1 and VLA-4 dependent T-lymphocyte adhesion to dermal fibroblasts stimulated with proinflammatory cytokines." *Immunol.* 89, 375 (1996)).

At present, there is a humanized monoclonal antibody (Antegren®, Athena Neurosciences/Elan) against VLA-4 in clinical development for the treatment of multiple sclerosis and Crohn's disease and a humanized monoclonal antibody (ACT-1®/LDP-02 LeukoSite) against $\alpha_4\beta_7$ in clinical development for the treatment of inflammatory bowel disease. There are also several VLA-4 antagonists in early clinical trials for treatment of asthma and arthritis. There still remains a need for potent low molecular weight inhibitors of VLA-4-, $\alpha_4\beta_7$- and/or $\alpha9\beta1$ dependent cell adhesion that have pharmacokinetic and pharmacodynamic properties suitable for use as human pharmaceuticals.

PCT Application No. WO98/53818 discloses compounds having activity as inhibitors of binding between VCAM-1 and cells expressing VLA-4, and having the formula:

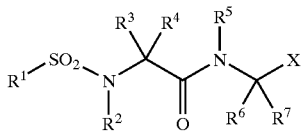

PCT Application No. WO98/53814 discloses compounds having activity as inhibitors of binding between VCAM-1 and cells expressing VLA-4, and having the formula:

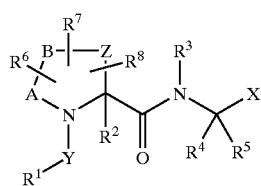

PCT Application No. WO98/53814 discloses compounds having activity as inhibitors of binding between VCAM-1 and cells expressing VLA-4, and having the formula:

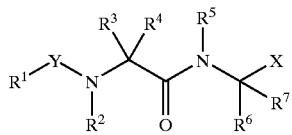

PCT Application Nos. WO99/06390, WO99/06431, WO99/06432, WO99/06433, WO99/06434, WO99/06435, WO99/06436, and WO99/06437 disclose compounds having activity as inhibitors of binding between VCAM-1 and cells expressing VLA-4, and having the formula:

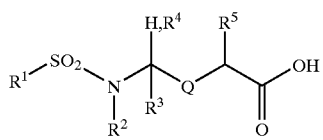

DETAILED DESCRIPTION OF THE INVENTION

The present invention provides compounds of Formula I:

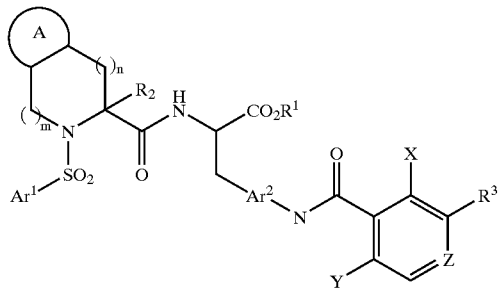

or a pharmaceutically acceptable salt thereof wherein:
Ring A is an aryl or heteroaryl ring,
wherein ring A is optionally substituted with one to four substituents independently selected from $R^b$;
X and Y are independently selected from
1) halogen,
2) $C_{1-3}$alkyl,
3) $C_{1-3}$alkoxy;
Z is
1) N,
2) $N^+$—$O^-$;
$R^1$ is
1) hydrogen,
2) $C_{1-10}$alkyl,
3) aryl-$C_{1-10}$alkyl;
$R^2$ is
1) hydrogen or
2) $C_{1-10}$alkyl,
wherein alkyl is optionally substituted with one to four substituents selected from a group independently selected from $R^c$;
$R^3$ is
1) hydrogen;
2) OH;
3) $OCH_3$; or
4) $NH_2$;
$R^a$ is
1) —$OR^d$,
2) —$NR^dS(O)_mR^e$,
3) —$NO_2$,
4) halogen
5) —$S(O)_pR^d$,
6) —$SR^d$,
7) —$S(O)_2OR^d$,
8) —$S(O)_mNR^dR^e$,
9) —$NR^dR^e$,
10) —$O(CR^fR^g)_nNR^dR^e$,
11) —$C(O)R^d$,
12) —$CO_2R^d$,
13) —$CO_2(CR^fR^g)_nCONR^dR^e$,
14) —$OC(O)R^d$,
15) —CN,
16) —$C(O)NR^dR^e$,
17) —$NR^dC(O)R^e$,
18) —$OC(O)NR^dR^e$,
19) —$NR^dC(O)OR^e$,
20) —$NR^dC(O)NR^dR^e$,
21) —$CR^d(N-OR^e)$, 22) CF$_3$,
23) —OCF$_3$,
24) C$_{3-8}$cycloalkyl, or
25) heterocyclyl;

wherein cycloalkyl and heterocyclyl are optionally substituted with one to four groups independently selected from R$^c$;

R$^b$ is
1) a group selected from R$^a$,
2) C$_{1-10}$alkyl,
3) C$_{2-10}$alkenyl,
4) C$_{2-10}$alkynyl,
5) Ar$^1$,
6) C$_{1-10}$alkyl-Ar$^1$, wherein alkyl, alkenyl, alkynyl, and Ar$^1$ are optionally substituted with one to four substituents selected from a group independently selected from R$^c$;

R$^c$ is
1) halogen,
2) amino,
3) carboxy,
4) C$_{1-4}$alkyl,
5) C$_{1-4}$alkoxy,
6) aryl,
7) aryl C$_{1-4}$alkyl,
8) hydroxy,
9) CF$_3$,
10) OC(O)C$_{1-4}$alkyl,
11) OC(O)NR$^f$R$^g$, or
12) aryloxy;

R$^d$ and R$^e$ are independently selected from hydrogen, C$_{1-10}$alkyl, C$_{2-10}$alkenyl, C$_{2-10}$alkynyl, Cy and Cy C$_{1-10}$alkyl, wherein alkyl, alkenyl, alkynyl and Cy are optionally substituted with one to four substituents independently selected from R$^c$; or R$^d$ and R$^e$ together with the atom(s) to which they are attached form a heterocyclic ring of 4 to 7 members containing 0–2 additional heteroatoms independently selected from oxygen, sulfur and N—R$^h$;

R$^f$ and R$^g$ are independently selected from hydrogen, C$_{1-10}$alkyl, Cy and Cy—C$_{1-10}$alkyl; or R$^f$ and R$^g$ together with the carbon to which they are attached form a ring of 5 to 7 members containing 0–2 heteroatoms independently selected from oxygen, sulfur and nitrogen;

R$^h$ is selected from R$^f$ and —C(O)R$^f$;

Cy is selected from cycloalkyl, heterocyclyl, aryl, and heteroaryl;

Ar$^1$ is selected from phenyl, pyridyl, pyridazinyl, pyrimidinyl, pyrazinyl and triazinyl each optionally substituted with one or two groups independently selected from R$^c$;

Ar$^2$ is 1,4-phenylene or 2,5-pyridylene;

p is 1 or 2;

m is 0, 1 or 2;

n is 0, 1 or 2.

In one embodiment of formula I, Ar$^1$ is pyridyl optionally substituted with C$_{1-3}$alkyl, or phenyl optionally substituted with one to two groups independently selected from halogen, C$_{1-3}$alkyl, carboxy, cyano, trifluoromethyl, and trifluoromethoxy. In one subset of this embodiment Ar$^1$ is 3-substituted phenyl optionally having a second substituent on the 5-position wherein the substituents are independently selected from chloro, fluoro, bromo, methyl, trifluoromethyl and trifluoromethoxy. In another subset Ar$^1$ is 3-pyridyl, 3-chlorophenyl, 3-carboxyphenyl, or 3,5-dichlorophenyl. Examples of Ar$^1$ include phenyl, 3-carboxylphenyl, 3-bromophenyl, 3-chlorophenyl, 3-fluorophenyl, 3-trifluoromethylphenyl, 3-trifluoromethoxyphenyl, 4-chlorophenyl, 4-methylphenyl, 3,5-dichlorophenyl, 3,4-dichlorophenyl, 3,5-bis(trifluoromethyl)phenyl, 3,5-dimethyl-phenyl, 3-pyridyl, 5-methyl-3-pyridyl.

In another embodiment of formula I, Ar$^2$ is 1,4-phenylene. Examples of Ar$^2$ include 1,4-phenylene.

In another embodiment of formula I one of X and Y is halogen and the other is selected from halogen, C$_{1-3}$alkyl and C$_{1-3}$alkoxy. In one subset of this embodiment one of X and Y is chloro and the other is chloro or methoxy. In another subset X and Y are each chloro.

One embodiment of formula I provides compounds of formula Ia:

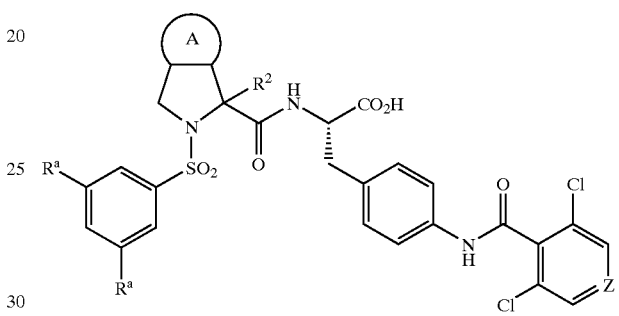

Ia wherein
Z is N or N+O$^-$;
Ring A is phenyl, or pyrazolyl;
R$^2$ is H or methyl;
R$^a$ is selected from hydrogen, halogen, cyano, or carboxyl; or
a pharmaceutically acceptable salt thereof.

In another aspect the present invention provides a method for the prevention or treatment of diseases, disorders, conditions or symptoms mediated by cell adhesion in a mammal which comprises administering to said mammal an effective amount of a compound of formula I.

In one embodiment said disease or disorder is selected from asthma, allergic rhinitis, multiple sclerosis, atherosclerosis, inflammatory bowel disease, rheumatoid arthritis, and organ transplantation.

In another aspect the present invention provides a method for preventing the action of VLA-4 in a mammal which comprises administering to said mammal a therapeutically effective amount of a compound of formula I.

Another aspect of the present invention provides a pharmaceutical composition which comprises a compound of formula I and a pharmaceutically acceptable carrier.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon—carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon—carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" includes fluorine, chlorine, bromine and iodine.

Optical Isomers-Diastereomers-Geometric Isomers-Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylanine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to antagonize the actions of VLA-4 and/or $\alpha 4\beta 7$ integrin makes them useful for preventing or reversing the symptoms, disorders or diseases induced by the binding of VLA-4 and or $\alpha 4\beta 7$ to their various respective ligands. Thus, these antagonists will inhibit cell adhesion processes including cell activation, migration, proliferation and differentiation. Accordingly, another aspect of the present invention provides a method for the treatment (including prevention, alleviation, amelioration or suppression) of diseases or disorders or symptoms mediated by VLA-4 and/or $\alpha 4\beta 7$ binding and cell adhesion and activation, which comprises administering to a mammal an effective amount of a compound of Formula I. Such diseases, disorders, conditions or symptoms are for example (1) multiple sclerosis, (2) asthma, (3) allergic rhinitis, (4) allergic conjunctivitis, (5) inflammatory lung diseases, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crohn's disease, (15) certain types of toxic and immune-based nephritis, (16) contact dermal hypersensitivity, (17) psoriasis, (18) tumor metastasis, (19) atherosclerosis, and (20) hepatitis.

The utilities of the present compounds in these diseases or disorders may be demonstrated in animal disease models that have been reported in the literature. The following are examples of such animal disease models:

i) experimental allergic encephalomyelitis, a model of neuronal demyelination resembling multiple sclerosis (for example, see T. Yednock et al., "Prevention of experimental autoimmune encephalomyelitis by antibodies against $\alpha_4\beta_1$ integrin." Nature, 356, 63 (1993) and E. Keszthelyi et al., "Evidence for a prolonged role of $\alpha_4$ integrin throughout active experimental allergic encephalomyelitis." Neurology, 47, 1053 (1996));

ii) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leucocyte recruitment and bronchial hyperresponsiveness in the guinea-pig." Eur. J. Pharmacol., 282, 243 (1995));

iii) adjuvant-induced arthritis in rats as a model of inflammatory arthritis (see C. Barbadillo et al., "Anti-VLA-4 mAb prevents adjuvant arthritis in Lewis rats." Arthr. Rheuma. (Suppl.), 36 95 (1993) and D. Seiffge, "Protective effects of monoclonal antibody to VLA-4 on leukocyte adhesion and course of disease in adjuvant arthritis in rats." J. Rheumatol., 23, 12 (1996));

iv) adoptive autoimmune diabetes in the NOD mouse (see J. L. Baron et al., "The pathogenesis of adoptive murine autoimmune diabetes requires an interaction between $\alpha_4$-integrins and vascular cell adhesion molecule-1.",J. Clin. Invest., 93, 1700 (1994), A. Jakubowski et al., "Vascular cell adhesion molecule-Ig fusion protein selectively targets activated α4-integrin receptors in vivo: Inhibition of autoimmune diabetes in an adoptive transfer model in nonobese diabetic mice." J. Immunol., 155, 938 (1995), and X. D. Yang et al., "Involvement of beta 7 integrin and mucosal addressin cell adhesion molecule-1 (MadCAM-1) in the development of diabetes in nonobese diabetic mice", Diabetes, 46, 1542 (1997));

v) cardiac allograft survival in mice as a model of organ transplantation (see M. Isobe et al., "Effect of anti-VCAM-1 and anti-VLA-4 monoclonal antibodies on cardiac allograft survival and response to soluble antigens in mice.", Tranplant. Proc., 26, 867 (1994) and S. Molossi et al., "Blockade of very late antigen-4 integrin binding to fibronectin with connecting segment-1 peptide reduces accelerated coronary arteripathy in rabbit cardiac allografts." J. Clin Invest., 95, 2601 (1995));

vi) spontaneous chronic colitis in cotton-top tamarins which resembles human ulcerative colitis, a form of inflammatory bowel disease (see D. K. Podolsky et al., "Attenuation of colitis in the Cotton-top tamarin by anti-$\alpha_4$ integrin monoclonal antibody.",J. Clin. Invest., 92, 372 (1993));

vii) contact hypersensitivity models as a model for skin allergic reactions (see T. A. Ferguson and T. S. Kupper, "Antigen-independent processes in antigen-specific immunity.", J. Immunol., 150, 1172 (1993) and P. L. Chisholm et al., "Monoclonal antibodies to the integrin a-4 subunit inhibit the murine contact hypersensitivity response." Eur. J. Immunol., 23, 682 (1993));

viii) acute nephrotoxic nephritis (see M. S. Mulligan et al., "Requirements for leukocyte adhesion molecules in nephrotoxic nephritis.", J. Clin. Invest., 91, 577 (1993));

ix) tumor metastasis (for examples, see M. Edward, "Integrins and other adhesion molecules involved in melanocytic tumor progression.", Curr. Opin. Oncol., 7, 185 (1995));

x) experimental autoimmune thyroiditis (see R. W. McMurray et al., "The role of α4 integrin and intercellular adhesion molecule-1 (ICAM-1) in murine experimental autoimmune thyroiditis." Autoimmunity, 23, 9 (1996);

xi) ischemic tissue damage following arterial occlusion in rats (see F. Squadrito et al., "Leukocyte integrin very late antigen-4/vascular cell adhesion molecule-1 adhesion pathway in splanchnic artery occlusion shock." Eur. J. Pharmacol., 318, 153 (1996; and xii) inhibition of TH2 T-cell cytokine production including IL-4 and IL-5 by VLA-4 antibodies which would attenuate allergic responses (J. Clinical Investigation 100, 3083 (1997).

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.005 mg to about 10 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

In the case where an aerosol composition is employed, a suitable dosage range is, e.g. from about 0.001 mg to about 1 mg of a compound of Formula I per kg of body weight per day, preferably from about 0.005 mg to about 0.5 mg per kg of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |

Water for injection to a total volume of 1 mL

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib, rofecoxib, and parecoxib; (h) inhibitors of phosphodiesterase type IV (PDE-IV); (i) antagonists of the chemokine receptors, especially CCR-1, CCR-2, and CCR-3; (j) cholesterol lowering agents such as HMG-CoA reductase inhibitors (lovastatin, simvastatin, pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone, pioglitazone, englitazone, MCC-555, BRL49653 and the like); (l) preparations of interferon beta (interferon beta-1a, interferon beta-1b); (m) anticholinergic agents such as muscarinic antagonists (ipratropium nad tiatropium); (n) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Abbreviations used in the following Schemes and Examples:

| | |
|---|---|
| 4-DMAP: | 4-dimethylaminopyridine |
| $Ac_2O$: | acetic anhydride |
| AcCN: | acetonitrile |
| $Ag_2O$: | silver(I) oxide |
| AIBN: | 2,2'-azobisisobutyronitrile |
| $BF_3$-$Et_2O$: | borontrifluoride etherate |
| $BH_3$-DMS: | borane dimethylsulfide complex |
| Bn: | benzyl |
| BOC: | tert-butoxycarbonyl |
| BOC-ON | 2-(tert-butoxycarbonyloxyimino)-2-phenylacetonitrile |
| BOP: | benzotriazol-1-yloxy-tris (dimethylamino)-phosphonium hexafluorophosphate |
| brine: | saturated sodium chloride solution |
| CBZ: | benzyloxycarbonyl |
| $Cy_3P$: | tricyclohexylphosphine |
| DBU: | 1,8-diazobicyclo[5.4.0]undec-7-ene |
| DCC: | dicyclohexylcarbodiimide |
| DIBAL-H: | diisobutylaluminum hydride |
| DIPEA: | N,N-diisopropylethylamine |
| DME: | 1,2-dimethoxyethane |
| DMF: | dimethylformamide |
| DMPU: | 1,3-dimethyl-3,4,5,6-tetrahydro-2(1H)-pyrimidinone |
| DMSO: | dimethylsulfoxide |
| EDC: | 1-ethyl-3-(3-dimethylaminopropyl)-carbodiimide hydrochloride |
| Et: | ethyl |
| $Et_2O$: | diethyl ether |

-continued

| | |
|---|---|
| EtOAc: | ethyl acetate |
| EtOH: | ethanol |
| FMOC: | 9-fluorenylmethoxylcarbonyl |
| g or gm: | gram |
| h or hr: | hr |
| HATU: | O-(7-azabenzotriazol-1-yl)-1,1,3,3-tetramethyluronium hexafluorophosphate |
| HBTU: | O-(benzotriazol-1-yl)-1,1,3,3-tetramethyluronium hexafluorophosphate |
| HOAc: | acetic acid |
| HOAt: | 1-hydroxy-7-azabenzotriazole |
| HOBt: | 1-hydroxybenzotriazole |
| HPLC: | high pressure liquid chromatography |
| in vacuo: | rotoevaporation |
| KOAc: | potassium acetate |
| LDA: | lithium diisopropylamide |
| LiHMDS: | lithium hexamethyldisilylamide |
| mCPBA: | meta-chloroperbenzoic acid |
| Me: | methyl |
| MeI: | methyl iodide |
| MeOH: | methanol |
| mg: | milligram |
| MHz: | megahertz |
| min: | minutes |
| mL: | milliliter |
| mmol: | millimole |
| MPLC: | medium pressure liquid chromatography |
| MS or ms: | mass spectrum |
| MsCl: | methanesulfonyl chloride |
| NBS: | N-bromosuccinimide |
| NMO: | 4-methyl-morpholine-N-oxide |
| $Pd_2dba_3$: | tris(dibenzylideneacetone) dipalladium(0) |
| Ph: | phenyl |
| $Ph_3P$: | triphenylphosphine |
| pTSA: | para-toluenesulfonic acid |
| PyBOP: | (benzotriazol-1-yloxy)tripyrrolidinophosphonium hexafluorophosphate |
| rt: | rt |
| TBAF: | tetrabutylammonium fluoride |
| TBSCl: | tert-butyldimethylsilyl chloride |
| $t-Bu_3P$: | tri-tert-butylphosphine |
| TEA: | triethylamine |
| TFA: | trifluoroacetic acid |
| THF: | THF |
| TLC: | thin layer chromatography |
| $TMSCHN_2$: | trimethylsiliyldiazomethane |
| TMSCl: | trimethylsilyl chloride |
| TMSI: | trimethylsilyl iodide |
| TPAP: | tetrapropylammonium perruthenate |
| TsCl: | para-toluene sulfonyl chloride |

Compounds of the present invention may be prepared by procedures illustrated in the accompanying schemes. In the first method (Scheme 1), a substituted pyridyl-4-carboxylic acid derivative A is treated with thionyl chloride to make the carboxylic acid chloride derivative which is subsequently reacted with a 4-amino-(L)-phenylalanine derivative to yield the amide B. The N-BOC-protecting group in B is removed with strong acid (TFA or HCl) to afford the free amine C. An appropriately substitued 1,3-dihydro-2H-isoindole-1-carboxylate D is sulfonylated with a substitued arylsulfonyl chloride in the presence of base (DIPEA or $Na_2CO_3$) to yield sulfonamide E which, if containing an ester protecting group, is treated with hydroxide to afford the free acid. Amine C and acid E are reacted together in the presence of an appropriate coupling agent (eg., PyBOP, HBTU/HOAt, premake the acid chloride of E, etc.) to afford amide F. The ester in F can be hydrolyzed with hydroxide (if $R_5$ is n-alkyl) or TFA or HCl (if $R_5$ is tert-butyl) to yield G.

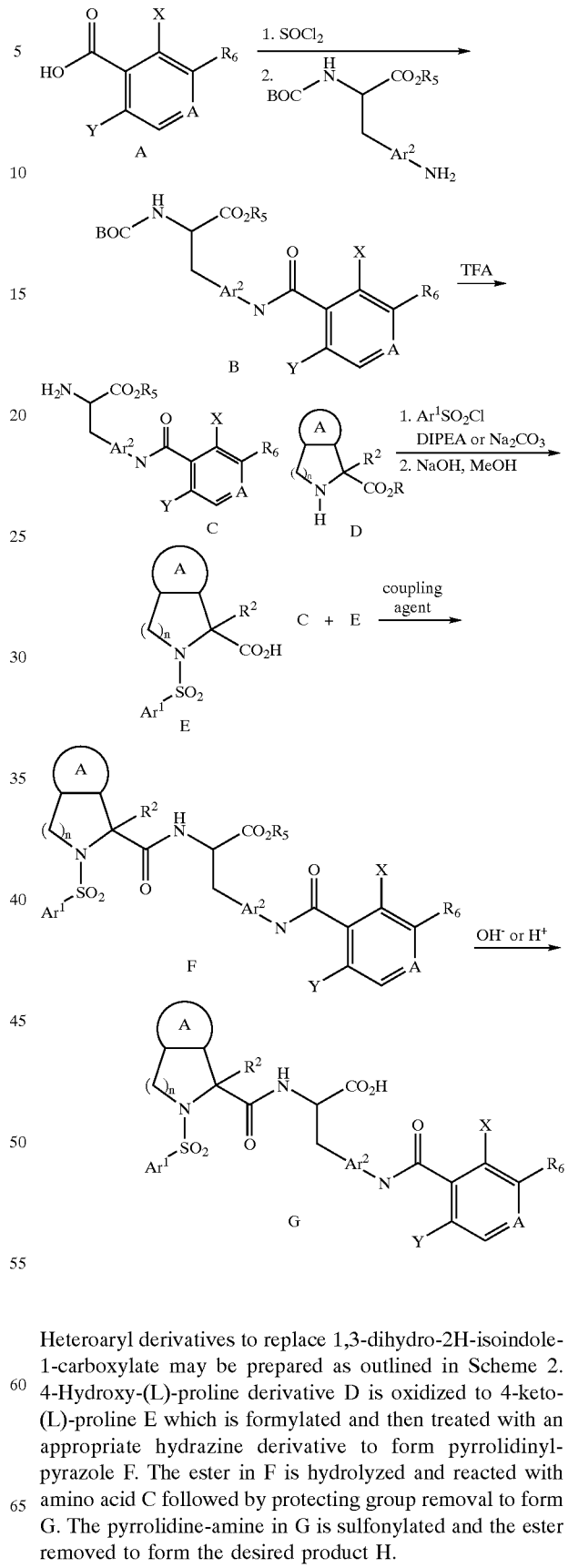

Scheme 1

Heteroaryl derivatives to replace 1,3-dihydro-2H-isoindole-1-carboxylate may be prepared as outlined in Scheme 2. 4-Hydroxy-(L)-proline derivative D is oxidized to 4-keto-(L)-proline E which is formylated and then treated with an appropriate hydrazine derivative to form pyrrolidinyl-pyrazole F. The ester in F is hydrolyzed and reacted with amino acid C followed by protecting group removal to form G. The pyrrolidine-amine in G is sulfonylated and the ester removed to form the desired product H.

Scheme 2

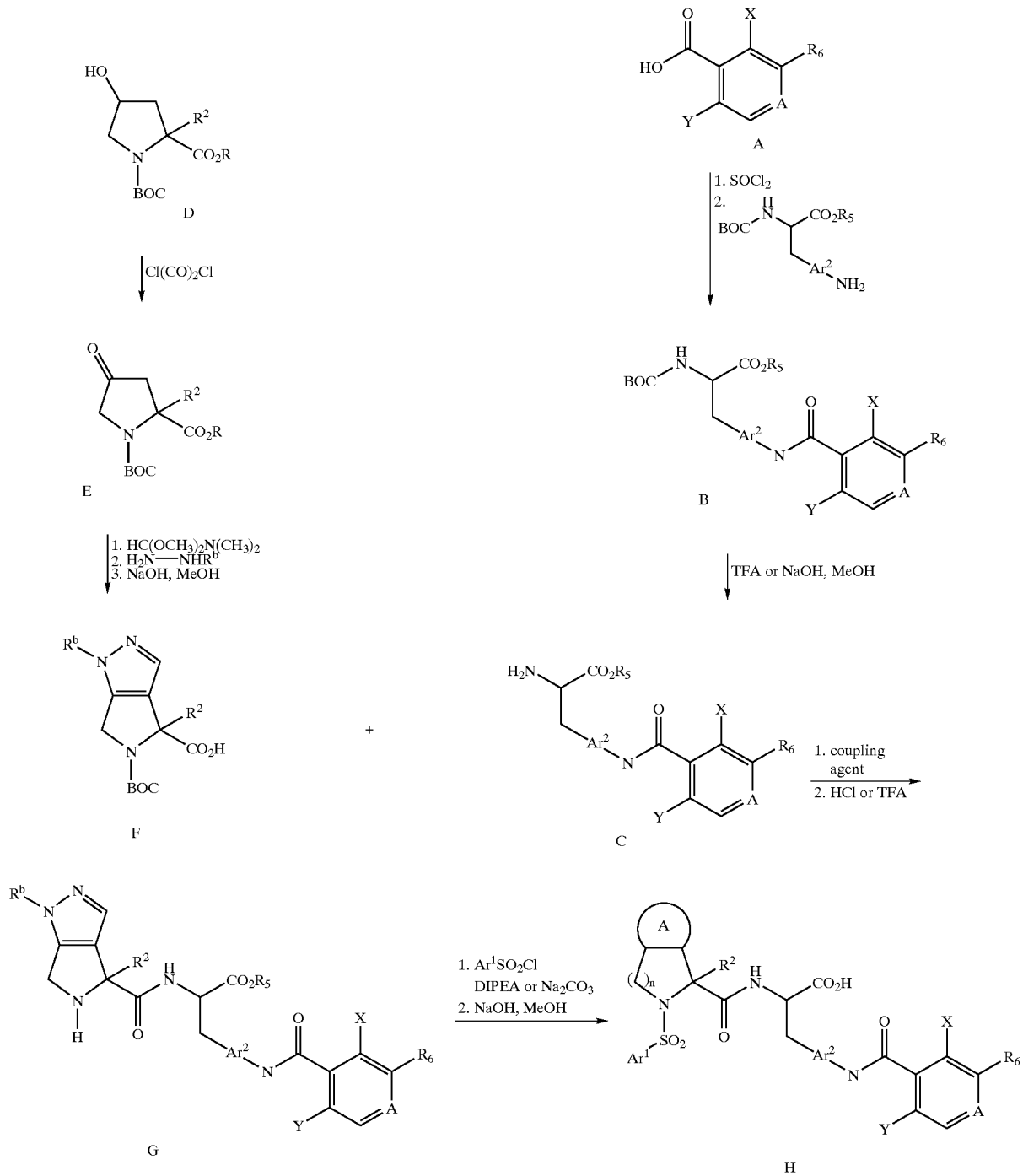

Compounds of the present invention may be prepared by procedures detailed in the following examples. The examples are provided to illustrative the present invention and are not to be construed as limiting its scope in any manner.

REFERENCE EXAMPLE 1

3,5-Dichloroisonicotinic acid

To a solution of 3,5-dichloropyridine (10.00 g, 67.57 mmol) in 70 mL of THF was added 35.4 mL of a 2.0 M solution of LDA in TiF at −78° C. The reaction was stirred for 1 h, then $CO_2$ gas was bubbled through the solution for 20 mins. The reaction was allowed to warm to rt over 1 h then quenched with 1N NaOH (100 mL) and washed with $Et_2O$ (50 mL). The aqueous layer was acidified with conc HCl which caused a precipitate to form. The precipitate was collected by filtration and recrystallized from EtOH to give the title compound as a pale yellow solid (7.1 g, 36.97 mmol, 55%).

$^1$H NMR (500 MHz, DMSO-$d_6$): δ8.73 (s, 2H).

REFERENCE EXAMPLE 2

4-((3,5-dichloroisonicotinoyl)amino)-(L)-phenylalanine, methyl ester hydrochloride

Step A N-(BOC)-4-((3',5'-dichloroisonicotinoyl)amino)-(L)-phenylalanine, methyl ester A slurry of 3,5-dichloroisonicotinic acid (3.1 g, 16.11 mmol) in 10 mL of $CH_2Cl_2$ was treated with DMF (50 µL) and thionyl chloride (1.23 mL, 16.91 mmol) and heated to reflux for 5 h. The reaction was concentrated to give a yellow oil. This oil was dissolved in 5 mL of $CH_2Cl_2$ and added to N-(BOC)-4-amino-(L)-phenylalanine, methyl ester (4.00 g, 14.39 mmol) and 4-methylmorpholine (2.7 mL, 24.21 mmol) in 25 mL of $CH_2Cl_2$ at 0° C. After stirring for 2 h at this temperature, the reaction was quenched with water (50 mL) and extracted into $CH_2Cl_2$ (3×100 mL). The combined organics were combined, dried over anhydrous MgSO4 and concentrated in vacuo to give a yellow solid. Trituration with $CH_2Cl_2$ gave 5.5 g of a while solid $^1$H NMR (500 MHz, CDCl$_3$): δ8.63 (s, 2H); 7.58 (d, J=8.2 Hz, 2H); 7.23 (d, J=8.2 Hz, 2H); 6.91 (d, J=8.4 Hz, 1H); 4.39 (m, 1H); 3.70 (s, 3H); 3.11 (m, 1H); 2.91 (m, 1H); 2.00 (s, 9H); MS m/e 468.20 (M$^+$).

Step B 4-((3',5'-dichloroisonicotinoyl)amino)-(L)-phenylalanine, methyl ester hydrochloride N-(BOC)-4-((3',5'-dichloroisonicotinoyl)amino)-(L)-phenylalanine, methyl ester (2.50 g, 5.34 mmol) was dissolved in EtOAc (40 mL) and treated with HCl (gas). Concentration in vacuo gave the title compound as a yellow solid (2.05 g, 4.59 mmol, 86%).

$^1$H NMR (500 MHz, CD$_3$OD): δ8.69 (s, 2H); 7.68 (d, J=8.5 Hz, 2H); 7.31 (m, J=8.5 Hz, 2H); 4.35 (t, J=6.9 Hz, 1H); 3.83 (s, 3H); 3.29 (m, 1H); 3.21 (m, 1H); MS m/e 368.13 (M$^+$).

REFERENCE EXAMPLE 3

4-(3',5'-Dichloroisonicotinoyl)amino-(L)-phenylalanine, tert-butyl ester

N$^α$-(BOC)-4-amino-(L)-phenylalanine, tert-butyl ester was reacted with 3',5'-dichloroisonicotinic acid according to the procedure described in Reference Example 2, Step A to afford N$_α$-(BOC)-4-[(3',5'-dichloroisonicotinoyl)amino]-(L)-phenylalanine, tert-butyl ester. The N$^α$-(BOC) protecting group was removed by the procedure of Lin et al (*Tetrahedron Lett* 2000, 41, 7013) to afford 4-(3',5'-dichloroisonicotinoyl)amino-(L)-phenylalanine, tert-butyl ester.

EXAMPLE 1

N-(N-[4-methylbenzenesulfonyl]-1,3-dihydro-2H-isoindole-1-carbonyl)-4-[(3',5'-dichloroisonicotinoyl)amino]-(L)-phenylalanine

Step A 1,3-Dihydro-2H-isoindole-1-carboxylic acid

N-BOC-1,3-dihydro-2H-isoindole-1-carboxylic acid (Neosystem, 0.5 g, 1.9 mmol) was dissolved in EtOAc and HCl gas was bubbled through the solution for a few seconds. The reaction mixture was stirred at rt for 10 minutes and then concentrated in vacuo to afford 1,3-dihydro-2H-isoindole-1-carboxylic acid, hydrochloride (0.31 gm, 100%) which was used without further purification in the subsequent reaction.

Step B N-[4-Methylbenzenesulfonyl]-1,3-dihydro-2H-isoindole-1-carboxylic acid 1,3-Dihydro-2H-isoindole-1-carboxylic acid, hydrochloride (0.31 g, 1.9 mmol), p-toluenesulfonyl chloride (0.4 g, 2.09 mmol), and Na$_2$CO$_3$ (0.403 g, 3,8 mmol) were dissolved in water (4 mL). The reaction mixture was stirred at rt for 20 hr. The residue was dissolved in water and washed with EtOAc. The aqueous layer was acidified with concentrated HCl and extracted with $CH_2Cl_2$ (2X). The organic layers were dried over anhydrous MgSO4 and concentrated in vacuo. The crude product was purified by HPLC to give N-[4-methylbenzenesulfonyl]-1,3-dihydro-2H-isoindole-1-carboxylic acid (0.047 g). MS m/e 318.1 (M$^+$)

Step C N-(N-[4-Methylbenzenesulfonyl]-1,3-dihydro-2H-isoindole-1-carbonyl)-4-[(3',5'-dichloroisonicotinoyl)amino]-(L)-phenylalanine, tert-butyl ester N-[4-Methylbenzenesulfonyl]-1,3-dihydro-2H-isoindole-1-carboxylic acid (0.047 g, 0.148 mmol), 4-[(3',5'-dichloroisonicotinoyl)amino]-(L)-phenylalanine, tert-butyl ester (0.067 g, 0.163 mmol), and PyBOP (0.092 g, 0.178 mmol) were dissolved in $CH_2Cl_2$ (1 mL) and DIPEA (0.07 mL, 0.37 mmol) was added. The reaction mixture was stirred at rt for about 20 hr. The residue was concentrated in vacuo, dissolved in AcCN:water (7:3), and purified by HPLC to yield N-(N-[4-methylbenzenesulfonyl]-1,3-dihydro-2H-isoindole-1-carbonyl)-4-[(3',5'-dichloroisonicotinoyl)amino]-(L)-phenylalanine, tert-butyl ester. MS m/e 709.3 (M$^+$)

Step D N-(N-[4-Methylbenzenesulfonyl]-1,3-dihydro-2H-isoindole-1-carbonyl)-4-[(3',5'-dichloroisonicotinoyl)amino]-(L)-phenylalanine N-(N-[4-Methylbenzenesulfonyl]-1,3-dihydro-2H-isoindole-1-carbonyl)-4-[(3',5'-dichloroisonicotinoyl)amino]-(L)-phenylalanine, tert-butyl ester (0.148 mmol) was dissolved in $CH_2Cl_2$ (0.5 mL) and TFA (0.5 mL). The reaction mixture was stirred at rt for 3.5 hr and then concentrated in vacuo. The residue was purified by HPLC to give N-(N-[4-methylbenzenesulfonyl]-1,3-dihydro-2H-isoindole-1-carbonyl)-4-[(3',5'-dichloroisonicotinoyl)amino]-(L)-phenylalanine (0.0709 g). MS m/e 653.3 (M$^+$)

EXAMPLE 2

N-[N-(3,5-Dichlorobenzenesulfonyl)-1,2,3,4-tetrahydroisoquinoline-3-carbonyl]-4-[(3',5'-dichloroisonicotinoyl)amino]-(L)-phenylalanine

Step A N-(3,5-Dichlorobenzenesulfonyl)-1,2,3,4-tetrahydroisoquinoline-3-carboxylic acid, methyl ester To a mixture of 1,2,3,4-tetrahydroisoquinoline-3-carboxylic acid, methyl ester hydrochloride (200 mg, 0.878 mmol) in a 1:1 mixture of $CH_2Cl_2$ and THF (2.5 mL each) was added dropwise DIPEA (0.88 mmol, 113 mg) followed by 3,5-dichlorobenzenesulfonyl chloride (0.922 mmol, 227 mg), a second equivalent of DIPEA and 4-DMAP (0.176 mmol, 22 mg). The reaction mixture was stirred at rt overnight when TLC (4:1 hexane:ethyl acetate) indicated disappearance of all starting material. The volatiles were removed in vacuo and the residue was purified by flash column chromatography on silica gel eluted with a gradient of hexane and ethyl acetate to yield N-(3,5-dichlorobenzenesulfonyl)-1,2,3,4-tetrahydroisoquinoline-3- carboxylic acid, methyl ester (282 mg, 80%) as a white foam, homogeneous by TLC (Rf=0.55, 4:1 hexane:ethyl acetate);

500 MHz $^1$H NMR (CDCl$_3$): δ3.24 (m, 2H), 3.54 (s, 3H), 4.47 (d, J=15 Hz, 1H), 4.74 (d, J=15 Hz, 1H), 5.01 (dd, J=3.7, 6 Hz, 1H), 7.08–7.27 (m, 4H), 7.56 (t, J=1.8 Hz, 1H), 7.73 (d, J=1.9 Hz, 2H).

Step B N-(3,5-Dichlorobenzenesulfonyl)-1,2,3,4-tetrahydroisoquinoline-3-carboxylic acid N-(3,5-Dichlorobenzenesulfonyl)-1,2,3,4-tetrahydroisoquinoline-3-carboxylic acid, methyl ester (100 mg, 0.25 mmol) was dissolved in 0.625 mL of MeOH and 0.625 mL of a 0.4 N solution of NaOH in MeOH was added. The resulting mixture was stirred overnight at rt. Volatiles were removed in vacuo and the residue was partitioned between 5% citric acid and CH$_2$Cl$_2$. The aqueous layer was extracted with CH$_2$Cl$_2$ (2X). The combined organic extracts were washed with brine, and dried over anhydrous Na$_2$SO$_4$. The residue obtained after filtration and evaporation of volatiles was purified by flash column chromatography on silica gel eluted with mixtures of CH$_2$Cl$_2$ and MeOH to afford N-(3,5-dichlorobenzenesulfonyl)-1,2,3,4-tetrahydroisoquinoline-3-carboxylic acid (85 mg) as a white foam, homogeneous by TLC (9:1 CH$_2$Cl$_2$:MeOH)

500 MHz $^1$H NMR (CD$_3$OD): δ3.14–3.24 (m, 2H), 4.47 (d, J=15 Hz, 1H), 4.73 (d, J=15 Hz, 1H), 4.94 (dd, J=3.4, 6.1 Hz, 1H), 7.06–7.18 (m, 4H), 7.65 (t, J=1.8 Hz, 1H), 7.79 (d, J=1.8 Hz, 2H).

Step C N-[N-(3,5-Dichlorobenzenesulfonyl)-1,2,3,4-tetrahydroisoquinoline-3-carbonyl]-4-(N-(3,5-dichloroisonicotinoyl)amino)-phenylalanine, methyl ester N-(3,5-Dichlorobenzenesulfonyl)-1,2,3,4-tetrahydroisoquinoline-3-carboxylic acid (25 mg, 0.0648 mmol) and 4-(N-(3,5-dichloroisonicotinoyl)amino)-phenylalanine, methyl ester hydrochloride (0.0648 mmol, 26 mg) were dissolved in 0.8 mL of CH$_2$Cl$_2$. DIPEA (0.163 mmol, 21 mg) was added followed by benzotriazole-1-yl-oxy-tris-pyrrodino-phosphonium hexafluorophosphate (0.072 mmole, 37 mg). After stirring at rt overnight, the volatiles were removed under reduced pressure and the residue was purified by flash column chromatography on silica gel eluted with a gradient of hexane and EtOAc to yield N-[N-(3,5-dichlorobenzenesulfonyl)-1,2,3,4-tetrahydroisoquinoline-3-carbonyl]-4-(N-(3,5-dichloroisonicotinoyl)amino)-phenylalanine, methyl ester (40 mg, 83%) as a white foam, homogeneous by TLC (Rf=0.35, 1:1 hexane:ethyl acetate). Mass spectrum (LC/MS ESI) m/e 737 (M+1)$^+$.

Step D N-[N-(3,5-Dichlorobenzenesulfonyl)-1,2,3,4-tetrahydroisoquinoline-3-carbonyl]-4-(N-(3,5-dichloroisonicotinoyl)amino)-phenylalanine N-[N-(3,5-Dichlorobenzenesulfonyl)-1,2,3,4-tetrahydroisoquinoline-3-carbonyl]-4-(N-(3,5-dichloroisonicotinoyl)amino)-phenylalanine, methyl ester (40 mg, 0.0543 mmol) was treated with a 0.2 N solution of NaOH in MeOH (0.0543 mmol, 0.272 mL). After stirring at rt for 6 h, TLC indicated disappearance of all starting material. The volatiles were removed under reduced pressure and the residue was partitioned between 5% citric acid and EtOAc. The aqueous layer was re-extracted with EtOAc (2X). The organic layers were combined and washed with brine and dried over anhydrous Na$_2$SO$_4$. The crude product was purified by flash column chromatography on silica gel eluted with a gradietn of CH$_2$Cl$_2$ and MeOH to afford N-[N-(3,5-dichlorobenzenesulfonyl)-1,2,3,4-tetrahydroisoquinoline-3-carbonyl]-4-(N-(3,5-dichloroisonicotinoyl)amino)-phenylalanine (28 mg, 72%) as a white foam, homogeneous by TLC (Rf=0.2 in 9:1 CH$_2$Cl$_2$:MeOH) Mass spectrum (LC/MS ESI) m/e 723 (M+1)$^+$.

500 MHz $^1$H NMR (CD$_3$OD): δ2.75–3.10 (m, 2H), 3.16–3.24 (m, 1H), 4.17 (d, J=16 Hz, 1H), 4.44–4.73 (m, 2H), 6.95–7.15 (m, 3H), 7.15–7.25 (m, 3H), 7.50–7.60 (m, 3H), 7.64–7.68(m, 2H), 8.63 (s, 2H).

EXAMPLE 3

N-(N-[(3,5-Dichlorobenzene)sulfonyl]-1,3-dihydro-2H-isoindole-1-carbonyl)-4-[(3',5'-dichloroisonicotinoyl)amino]-(L)-phenylalanine Step A N-[(3,5-Dichlorobenzene)sulfonyl]-1,3-dihydro-2H-isoindole-1-carboxylic acid N-[(3,5-Dichlorobenzene)sulfonyl]-1,3-dihydro-2H-isoindole-1-carboxylic acid was prepared (1.3 g, 81%) from 1,3-dihydro-2H-isoindole-1-carboxylic acid, hydrochloride salt from Example 1, Step A (0.85 g, 4.2 mmol) and 3,5-dichlorobenzenesulfonyl chloride according to the procedure described in Example 1, Step B (an additional 0.5 equivalent of Na$_2$CO$_3$ was used).

Step C N-(N-[(3,5-Dichlorobenzene)sulfonyl]-1,3-dihydro-2H-isoindole-1-carbonyl)-4-[(3',5'-dichloroisonicotinoyl)amino]-(L)-phenylalanine, tert-butyl ester N-[(3,5-Dichlorobenzene)sulfonyl]-1,3-dihydro-2H-isoindole-1-carboxylic acid (0.080 g, 0.22 mmol) was reacted with 4-(3',5'-dichloroisonicotinoyl)amino-(L)-phenylalanine, tert-butyl ester according to the procedure described in Example 1, Step C to afford N-(N-[(3,5-dichlorobenzene)sulfonyl]-1,3-dihydro-2H-isoindole-1-carbonyl)-4-[(3',5'-dichloroisonicotinoyl)amino]-(L)-phenylalanine, tert-butyl ester (0.084 g, 51%).

$^1$H NMR (400 MHz, CD$_3$OD): δ (mixture of two isomers) 8.64/8.62 (s, 2H); 7.85/7.81 (d, 2H); 7.74 (t, 1H); 7.61 (d, 2H); 7.51 (d, 2H); 7.32–7.10 (m, 4H); 5.44 (dd, 1H), 4.86–4.59 (m, 3 H); 3.30–2.92 (m, 2H); 1.44/1.42 (s, 9H). MS: calculated for C34H30Cl4N4O6S 762, observed m/e 707 (M+H–C$_4$H$_9$)$^+$.

Step D N-(N-[(3,5-Dichlorobenzene)sulfonyl]-1,3-dihydro-2H-isoindole-1-carbonyl)-4-[(3',5'-dichloroisonicotinoyl)amino]-(L)-phenylalanine To a solution of N-(N-[(3,5-dichlorobenzene)sulfonyl]-1,3-dihydro-2H-isoindole-1-carbonyl)-4-[(3',5'-dichloroisonicotinoyl)amino]-(L)-phenylalanine, tert-butyl ester (0.084 g, 0.11 mmol) in CH$_2$Cl$_2$ (3.0 mL) was added TFA (0.83 mL). After stirring at rt overnight, the reaction mixture was concentrated in vacuo to dryness to yield N-(N-[(3,5-dichlorobenzene)sulfonyl]-1,3-dihydro-2H-isoindole-1-carbonyl)-4-[(3',5'-dichloroisonicotinoyl)amino]-(L)-phenylalanine (0.075 g, 100%). 1H NMR (400 MHz, CD$_3$OD): δ (mixture of two isomers) 8.64/8.62 (s, 2H); 7.83/7.79 (d, 2H); 7.71 (t, 1H); 7.59 (d, 2H); 7.50 (d, 2H); 7.35–7.10 (m, 4 H); 5.46 (dd, 1H), 4.90–4.70 (m, 3 H); 3.40–2.96 (m, 2H). MS: calculated for C30H22Cl4N4O6S 706, observed m/e 707 (M+H)$^+$.

EXAMPLE 4

N-(N-[(3,5-Dichlorobenzene)sulfonyl]-1,3-dihydro-1-methyl-2H-isoindole-1-carbonyl)-4-[(3',5'-dichloroisonicotinoyl)amino]-(L)-phenylalanine Step A N-BOC-1,3-dihydro-2H-isoindole-1-carboxylic acid, methyl ester To a solution of N-BOC-1,3-dihydro-2H-isoindole-1-carboxylic acid (SNPE, 10 g, 38 mmol) in CH$_2$Cl$_2$ (100 mL)

and MeOH (100 mL) at 0° C. was added trimethylsilyldiazomethane dropwise until the yellow color persisted. After stirring at rt for 15 min, the reaction mixture was concentrated in vacuo to dryness, and the residue was azeotroped with toluene to yield N-BOC-1,3-dihydro-2H-isoindole-1-carboxylic acid, methyl ester which was used without further purification.

Step B N-BOC-1,3-dihydro-1-methyl-2H-isoindole-1-carboxylic acid, methyl ester

To a solution N-BOC-1,3-dihydro-2H-isoindole-1-carboxylic acid, methyl ester (38 mmol) and MeI (10 mL, 160 mmol) in 150 mL of anhydrous THF at −30° C. was added LDA (Aldrich, 1.5 M in cyclohexane, 51 mL, 76.5 mmol). The reaction was allowed to warm up to rt over 4 hr. The reaction was cooled to −30° C., and was quenched with saturated aqueous solution of $NH_4Cl$ (50 mL). The resulting mixture was partitioned between EtOAc and brine, and the product was extracted with EtOAc (3×100 mL). The combined extracts were dried over anhydrous $MgSO_4$ and concentrated in vacuo. The residue was purified by flash column chromatography on silica gel eluted with 10:1 to 5:1 hexane/ether to afford N-BOC-1,3-dihydro-1-methyl-2H-isoindole-1-carboxylic acid, methyl ester.

$^1$H NMR (500 MHz, $CD_3OD$): δ (mixture of rotamers) 7.40–7.10 (m, 4 H); 4.80–4.64 (m, 2H); 3.65/3.62 (s, 3H); 1.84/1.82 (s, 3H); 1.51/1.47 (s, 9H).

Step C 1,3-Dihydro-1-methyl-2H-isoindole-1-carboxylic acid, methyl ester, hydrochloride To a sample of N-BOC-1,3-dihydro-1-methyl-2H-isoindole-1-carboxylic acid, methyl ester (0.50 g, 1.7 mmol) was added HCl in dioxane (4 M, 5.0 mL). After stirring at rt for 1 hr, the reaction mixture was concentrated in vacuo, and the residue was triturated with $Et_2O$ and was concentrated to dryness to yield 1,3-dihydro-1-methyl-2H-isoindole-1-carboxylic acid, methyl ester, hydrochloride (0.40 g, 100%) which was used in the subsequent reaction without purification.

Step D N-[(3,5-Dichlorobenzene)sulfonyl]-1,3-dihydro-1-methyl-2H-isoindole-1-carboxylic acid, methyl ester To a solution of 1,3-dihydro-1-methyl-2H-isoindole-1-carboxylic acid, methyl ester, hydrochloride (Step C, 0.20 g, 0.88 mmol) in $CH_2Cl_2$ (1 mL) and THF (1 mL) at 0° C. was added DIPEA (0.46 mL, 2.6 mmol), 4-DMAP (0.011 g, 0.088 mmol) and 3,5-dichlorobenzenesulfonyl chloride (0.22 g, 0.88 mmol). The reaction was allowed to warm up to rt overnight. The reaction mixture was concentrated in vacuo to dryness, and the residue was purified by flash column chromatography on silica gel eluted with 20:1 hexane/EtOAc to yield N-[(3,5-dichlorobenzene)sulfonyl]-1,3-dihydro-1-methyl-2H-isoindole-1-carboxylic acid, methyl ester (0.18 g, 50%).

$^1$H NMR (400 MHz, $CD_3OD$): δ7.84 (d, 2H); 7.77 (t, 1H); 7.40–7.18 (m, 4H); 4.77 (ABq, 2H); 3.62 (s, 3H); 1.90 (s, 3H).

Step E N-[(3,5-Dichlorobenzene)sulfonyl]-1,3-dihydro-1-methyl-2H-isoindole-1-carboxylic acid N-[(3,5-Dichlorobenzene)sulfonyl]-1,3-dihydro-1-methyl-2H-isoindole-1-carboxylic acid, methyl ester (0.17 g, 0.43 mmol) was reacted with NaOH in MeOH according to the procedure described in Example 2, Step B to afford N-[(3,5-dichlorobenzene)sulfonyl]-1,3-dihydro-1-methyl-2H-isoindole-1-carboxylic acid (0.17 g, 100%).

$^1$H NMR (400 MHz, $CD_3OD$): δ7.88 (d, 2H); 7.75 (t, 1H); 7.40–7.20 (m, 4H); 4.75 (ABq, 2H); 1.90 (s, 3H).

Step F N-(N-[(3,5-Dichlorobenzene)sulfonyl]-1,3-dihydro-1-methyl-2H-isoindole-1-carbonyl)-4-[(3', 5'-dichloroisonicotinoyl)amino]-(L)-phenylalanine, methyl ester N-[(3,5-Dichlorobenzene)sulfonyl]-1,3-dihydro-1-methyl-2H-isoindole-1-carboxylic acid (0.10 g, 0.26 mmol) was coupled to 4-[(3',5'-dichloro-isonicotinoyl)amino]-(L)-phenylalanine, methyl ester according to the procedure described in Example 1, Step C to afford N-(N-[(3,5-dichlorobenzene)sulfonyl]-1,3-dihydro-1-methyl-2H-isoindole-1-carbonyl)-4-[(3',5'-dichloroisonicotinoyl)amino]-(L)-phenylalanine, methyl ester as a mixture of two diastereomers (0.12 g, 61%). The mixture was separated into two pure diastereomers on a Chiralpak AS HPLC column eluted with 20% ethanol/hexane.

Faster eluting isomer:
$^1$H NMR (500 MHz, $CD_3OD$): δ8.65 (s, 2H); 7.88 (d, J=2.0 Hz, 2H); 7.76 (t, J=2.0 Hz, 1H); 7.37 (d, J=8.5 Hz, 2H); 7.36–7.30 (m, 3 H); 7.08–7.05 (m, 1H); 6.83 (d, J=8.5 Hz, 2H); 4.74 (dd, J=8.0, 5.0 Hz, 1H); 4.70 (s, 2 H); 3.75 (s, 3H); 3.10 (dd, J=14.0, 5.0 Hz, 1 H); 2.97 (dd, J=14.0, 8.0 Hz, 1H); 1.84 (s, 3H). MS: m/e 735 $(M+H)^+$.

Slower eluting isomer:
$^1$H NMR (500 MHz, $CD_3OD$): δ8.65 (s, 2H); 7.84 (d, J=2.0 Hz, 2H); 7.74 (t, J=2.0 Hz, 1H); 7.55 (d, J=8.5 Hz, 2H); 7.26–7.19 (m, 5 H); 6.73 (d, J=7.5 Hz, 1H); 4.70 (ABq, 2 H); 4.66 (dd, J=9.5, 5.0 Hz, 1H); 3.69 (s, 3H); 3.24 (dd, J=14.0, 5.0 Hz, 1 H); 3.10 (dd, J=14.0, 9.5 Hz, 1H); 1.87 (s, 3H). MS: m/e 735 $(M+H)^+$.

Step G N-(N-[(3,5-Dichlorobenzene)sulfonyl]-1,3-dihydro-1-methyl-1H-isoindole-1-carbonyl)-4-[(3', 5'-dichloroisonicotinoyl)amino]-(L)-phenylalanine The two diastereomers of N-(N-[(3,5-dichlorobenzene)sulfonyl]-1,3-dihydro-1-methyl-2H-isoindole-1-carbonyl)-4-[(3',5'-dichloroisonicotinoyl)amino]-(L)-phenylalanine methyl ester were separately reacted with NaOH in MeOH according to the procedure described in Example 2, Step D with following modifications: the crude reaction mixture was partitioned between brine, 1 M HCl and EtOAc. The product was extracted with EtOAc (3X), and the combined extracts were dried over anhydrous $MgSO_4$, filtered, and concentrated in vacuo to afford the respective diastereomers of N-(N-[(3,5-dichlorobenzene)sulfonyl]-1,3-dihydro-1-methyl-1H-isoindole-1-carbonyl)-4-[(3',5'-dichloro-isonicotinoyl)amino]-(L)-phenylalanine.

Isomer from the faster eluting isomer of Step F:
$^1$H NMR (500 MHz, $CD_3OD$): δ8.64 (s, 2H); 7.90 (d, J=2.0 Hz, 2H); 7.75 (t, J=2.0 Hz, 1H); 7.40–7.30 (m, 5 H); 7.15 (d, J=7.0 Hz, 1H); 6.78 (d, J=8.5 Hz, 2H); 4.73 (dd, J=13.0 Hz, 1H); 4.73–4.68 (m, 1H); 4.64 (d, J=13.0 Hz, 1H); 3.10 (dd, J=13.5, 4.5 Hz, 1 H); 2.98 (dd, J=13.5, 7.0 Hz, 1H); 1.87 (s, 3H). MS: m/e 721 $(M+H)^+$.

Isomer from the slower eluting isomer of Step F:
$^1$H NMR (500 MHz, $CD_3OD$): δ8.65 (s, 2H); 7.84 (br s, 2H); 7.72 (br s, 1H); 7.54 (d, J=8.0 Hz, 2H); 7.30–7.16 (m, 5 H); 6.73 (d, J=7.5 Hz, 1H); 6.70 (s, 2H); 4.65 (m, 1H); 3.26 (dd, J=13.5, 4.5 Hz, 1 H); 3.11 (dd, J=13.5, 9.5 Hz, 1H); 1.90 (s, 3H). MS: m/e 721 $(M+H)^+$.

The following compounds were prepared from 1,3-dihydro-1-methyl-2H-isoindole-1-carboxylic acid, methyl ester, hydrochloride according to the procedures described in Example 4, substituting 3-pyridine-sulfonyl chloride or 3-cyanobenzene-sulfonyl chloride for 3,5-dichlorobenzene-sulfonyl chloride in Step D. For Example 6, two equivalents of NaOH were employed in Step G to hydrolyze the ester and nitrile.

| Example No. | Name | Mass Spectrum m/e |
|---|---|---|
| 5 | N-[N-(3-pyridine-sulfonyl)-1,3-dihydro-1-methyl-1H-isoindole-1-carbonyl]-4-[(3',5'-dichloroisonicotinoyl)-amino]-(L)-phenylalanine | 654 |
| 6 | N-(N-[(3-carboxybenzene)sulfonyl]-1,3-dihydro-1-methyl-1H-isoindole-1-carbonyl)-4-[(3',5'-dichloroisonicotinoyl)-amino]-(L)-phenylalanine | 696 |

EXAMPLE 7

N-[5-(3,5-Dichlorobenzensulfonyl)-1-ethyl-1,4,5,6-tetrahydropyrrolo[3,4-c]pyrazole-4 (S)-carbonyl]-4-(3',5'-dichloroisonicotinoyl)amino-(L)-phenylalanine Step A N-(BOC)-4-oxo-(L)-proline, methyl ester A solution of 3.5 mL (40.2 mmol) of oxalyl chloride in 20 mL of $CH_2Cl_2$ was cooled in a −78° C. bath and 3.5 mL (49.3 mmol) of dry DMSO was added. After 30 min, a solution of 5.31 g (23 mmol) of N-(BOC)-4-hydroxy-(L)-proline, methyl ester was added. A precipitate developed during the addition. After 30 min at −78° C., 15 mL (107 mmol) of TEA was added. Another 30 mL of $CH_2Cl_2$ was added to the reaction mixture to facilitate stirring and cold bath was removed. After 1.5 hr the solution was partitioned between $CH_2Cl_2$ and water. The organic layer was washed with water, 1.2 N HCl, brine then dried over anydrous $Na_2SO_4$. The filtrate was concentrated in vacuo and the residue was purified by flash column chromatography on silica gel eluted with a gradient of 20–40% EtOAc/hexane to yield N-(BOC)-4-oxo-(L)-proline, methyl ester (4.56 g).

$^1$H NMR (500 MHz, $CDCl_3$): δ1.48 (s, 9H), 2.59 (d, 1H), 2.95 (m, 1H), 3.78 (s, 3H), 3.9 (m, 2H), 4.72 and 4.82 (2d, 1H).

Step B 5-(BOC)-1-Ethyl-1,4,5,6-tetrahydropyrrolo[3,4-c]pyrazole-4(S)-carboxylic acid, methyl ester To 0.25 g (1.02 mmol) of N-(BOC)-4-oxo-(L)-proline, methyl ester, 0.5 mL (3.76 mmol) of N,N-dimethylformaminde dimethyl acetal was added and stirred for 30 min. The dark solution was diluted with EtOAC and washed with water, brine, dried over anhydrous $Na_2SO_4$ and concentrated in vacuo. The residue was dissolved in 3 mL of MeOH and 0.3 mL of aqueous ethylhydrazine (35%) was added. After 2 hr, the reaction was concentrated in vacuo and the residue was partitioned between EtOAc and water. The organic layer was washed with brine, dried over anhydrous $Na_2SO_4$ and concentrated in vacuo. The residue was purified by flash column chromatogrphy on silica gel eluted with a gradient of 50–100% EtOAc/hexane to yield 5-(BOC)-1-ethyl-1,4,5,6-tetrahydropyrrolo[3,4-c]pyrazole-4(S)-carboxylic acid, methyl ester (0.12 g).

NMR (500 MHz, $CDCl_3$): δ1.42 (t, 3H), 1.39 (s, 9H), 3.17 (q, 2H), 3.78 9s, 3H), 3.5–4.4 (m, 3H), 6.73 (s, 1H).

Step C 5-(BOC)-1-Ethyl-1,4,5,6-tetrahydropyrrolo[3,4-c]pyrazole-4(S)-carbonyl)-4-(3',5'-dichloroisonicotinoyl)amino-(L)-phenylalanine, methyl ester A solution of 0.12 g (0.406 mmol) of 5-(BOC)-1-ethyl-1,4,5,6-tetrahydropyrrolo[3,4-c]pyrazole-4(S)-carboxylic acid, methyl ester in 2 mL of MeOH was treated with 1 mL of 1N aqueous NaOH. After sonicating the solution for 15 min, it was acidified (pH 2) with 1.2 N HCl and concentrated in vacuo. The residue was diluted with EtOAc and washed with water and brine. The solution was dried over anhydrous $Na_2SO_4$ and concentrated in vacuo leaving 0.11 g of a residual oil. This oil was dissolved in 2 mL of $CH_2Cl_2$, 0.16 g (0.395 mmol) of 4-(3',5'-dichloro-isonicotinoyl)amino-(L)-phenylalanine, methyl ester, hydrochloride and 0.17 mL (1.21 mmol) of TEA were added. After all the salt had dissolved, 0.21 g (0.4 mmol) of benzotriazole-1-yl-oxy-tris-pyrrolidino-phosphonium hexafluorophosphate (PyBOP) was added. After stirring for 4 hr, the reaction was partitioned between $CH_2Cl_2$ and water. The organic layer was washed with brine, dried over anhydrous $Na_2SO_4$ and concentrated in vacuo. The residue was purified by flash column chromatography on silica gel eluted with EtOAc and 5% methanol-EtOAc to afford 5-(BOC)-1-ethyl-1,4,5,6-tetrahydropyrrolo[3,4-c]pyrazole-4(S)-carbonyl)-4-(3',5'-dichloroisonicotinoyl)amino-(L)-phenylalanine, methyl ester (99 mg).

$^1$H NMR (500 MHz, $CDCl_3$): δ1.44 (s, 9H), 1.47 (t, 3H), 3–3.25 (m, 2H), 3.77 (s, 3H), 4.1 (m, 2H), 4.4–5.3 (m, 4H), 6.4–7.4 (m, 5H), 8.1 (br s, 1H), 8.56 (s, 2H).

Step D 1-Ethyl-1,4,5,6-tetrahydropyrrolo[3,4-c]pyrazole-4(S)-carbonyl)-4-(3',5'-dichloroisonicotinoyl)amino-(L)-phenylalanine, methyl ester, hydrochloride A solution of 99 mg (0.16 mmol) of 5-(BOC)-1-ethyl-1,4,5,6-tetrahydropyrrolo[3,4-c]pyrazole-4(S)-carbonyl)-4-(3',5'-dichloroisonicotinoyl)amino-(L)-phenylalanine, methyl ester in 1 mL of EtOAc was treated with 3 mL of EtOAc saturated with HCl gas. A precipitate was formed immediately. After 1 hr the solid was filtered, washed with EtOAc and dried to yield 1-ethyl-1,4,5,6-tetrahydropyrrolo[3,4-c]pyrazole-4(S)-carbonyl)-4-(3',5'-dichloroisonicotinoyl)amino-(L)-phenylalanine, methyl ester, hydrochloride (82 mg).

$^1$H NMR (500 MHz, $CD_3OD$): δ1.43 (t, 3H), 3.07 (m, 1H), 3.27 (m, 1H), 3.7 (s, 3H), 4.15 (q, 2H), 4.63 (Abq, 2H), 4.79 (m, 1H), 5.34 (s, 1H), 7.29 (d, 2H), 7.46 (s, 1H), 7.61 (d, 2H), 8.67 (s, 2H), 9.13 (d, 1H).

Step E N-[(5-(3,5-Dichlorobenzensulfonyl)-1-ethyl-1,4,5,6-tetrahydro-pyrrolo[3,4-c]pyrazole-4 (S)-carbonyl]-4-(3',5'-dichloroisonicotinoyl)-amino-(L)-phenylalanine, methyl ester To a solution of 50 mg (0.078 mmol) of 1-ethyl-1,4,5,6-tetrahydro-pyrrolo[3,4-c]pyrazole-4(S)-carbonyl)-4-(3',5'-dichloroisonicotinoyl)amino-(L)-phenylalanine, methyl ester, hydrochloride, in 1 mL of $CH_2Cl_2$ and 1 mL of water, 22 mg (0.09 mmol) of 3,5-dichlorobenzenesulfonyl chloride and 22 mg (0.21 mmol) of $Na_2CO_3$ were added. After stirring the reaction overnight, another 10 mg (0.09 mmol) of $Na_2CO_3$ and 10 mg (0.04 mmol) of 3,5-dichlorobenzenesulfonyl chloride were added and stirred for 6 hr. The layers were separated and the $CH_2Cl_2$ layer was concentrated in vacuo and the residue purified by preparative TLC on silica eluted with 5% MeOH/EtOAc to afford N-[(5-(3,5-dichlorobenzensulfonyl)-1-ethyl-1,4,5,6-tetrahydropyrrolo[3,4-c]pyrazole-4(S)-carbonyl]-4-(3',5'-dichloroisonicotinoyl)amino-(L)-phenylalanine, methyl ester (47 mg).

$^1$H NMR (500 MHz, CDCl$_3$): δ1.45 (t, 3H), 3.08 (m, 1H), 3.21 (m, 1H), 3.83 (s, 3H), 4.13 (q, 2H), 4.45 and 4.6 (Abq, 2H), 4.86 (m 1H), 5.12 (s, 1H), 6.8–7.8 (m, 9H), 8.59 (s, 2H). LC-MS: m/e 741 (M+1).

Step F N-[(5-(3,5-dichlorobenzensulfonyl)-1-ethyl-1,4,5,6-tetrahydropyrrolo-[3,4-c]pyrazole-4(S)-carbonyl]-4-(3',5'-dichloroisonicotinoyl)amino-(L)-phenylalanine A solution of 47 mg (0.063 mmol) of N-[(5-(3,5-dichlorobenzensulfonyl)-1-ethyl-1,4,5,6-tetrahydropyrrolo[3,4-c]pyrazole-4(S)-carbonyl]-4-(3',5'-dichloroisonicotinoyl)amino-(L)-phenylalanine, methyl ester in 2 mL of MeOH and 0.5 mL of water was treated with 7 mg (0.167 mmol) of LiOH—H$_2$O. After stirring for 2 hr the solution was acidified (pH 2) with 1.2 N HCl and concentrated in vacuo. The residue purified by preparative TLC on silica eluted with 94.5:5:0.5 CH$_2$Cl$_2$:MeOH:HOAc to yield N-[(5-(3,5-dichlorobenzensulfonyl)-1-ethyl-1,4,5,6-tetrahydropyrrolo[3,4-c]pyrazole-4(S)-carbonyl]-4-(3',5'-dichloroisonicotinoyl)amino-(L)-phenylalanine (35 mg) as a solid. LC-MS: m/e 727 (M+1).

EXAMPLE 8

N-[(5-(3,5-dichlorobenzensulfonyl)-1-methyl-1,4,5,6-tetrahydropyrrolo[3,4-c]pyrazole-4 (S)-carbonyl]-4-(3',5'-dichloroisonicotinoyl)amino-(L)-phenylalanine N-[(5-(3,5-dichlorobenzensulfonyl)-1-methyl-1,4,5,6-tetrahydro-pyrrolo[3,4-c]pyrazole-4(S)-carbonyl]-4-(3',5'-dichloroisonicotinoyl)amino-(L)-phenylalanine was prepared by the method described in Example 7 but substituting methylhydrazine for ethylhydrazine in step B. LC-MS: m/e 713 (M+1).

EXAMPLE 9

N-[(5-(3,5-dichlorobenzensulfonyl)-1,4,5,6-tetrahydropyrrolo[3,4-c]pyrazole-4 (S)-carbonyl]-4-(3',5'-dichloroisonicotinoyl)amino-(L)-phenylalanine N-[(5-(3,5-dichlorobenzensulfonyl)-1,4,5,6-tetrahydropyrrolo[3,4-c]-pyrazole-4 (S)-carbonyl]-4-(3',5'-dichloroisonicotinoyl)amino-(L)-phenylalanine was prepared by the method described in Example 7 but substituting hydrazine for ethylhydrazine in step B. LC-MS: m/e 699 (M+1).

EXAMPLE 10

Antagonism of VLA-4 Dependent Binding to VCAM-Ig Fusion Protein

Step A Preparation of VCAM-Ig

The signal peptide as well as domains 1 and 2 of human VCAM (GenBank Accession no. M30257) were amplified by PCR using the human VCAM cDNA (R & D Systems) as a template. The resulting PCR product of 650 bp was digested with EcoRI and BclI and ligated to expression vector pIg-Tail (R & D Systems, Minneapolis, Minn.) digested with EcoRI and BamHI. The pIg-Tail vector contains the genomic fragment which encodes the hinge region, CH2 and CH3 of human IgG1 (GenBank Accession no. Z17370). The DNA sequence of the resulting VCAM fragment was verified using Sequenase (US Biochemical, Cleveland, Ohio). The fragment encoding the entire VCAM-Ig fusion was subsequently excised from pIg-Tail with EcoRI and NotI and ligated to pCI-neo (Promega, Madison, Wis.) digested with EcoRI and NotI. The resulting vector, designated pCI-neo/VCAM-Ig was transfected into CHO-K1 (ATCC CCL 61) cells using calcium-phosphate DNA precipitation (Specialty Media, Lavalette, N.J.). Stable VCAM-Ig producing clones were selected according to standard protocols using 0.2–0.8 mg/ml active G418 (Gibco, Grand Island, N.Y.), expanded, and cell supernatants were screened for their ability to mediate Jurkat adhesion to wells previously coated with 1.5 mg/ml (total protein) goat anti-human IgG (Sigma, St. Louis, Mo.). A positive CHO-K1/VCAM-Ig clone was subsequently adapted to CHO-SFM serum-free media (Gibco) and maintained under selection for stable expression of VCAM-Ig. VCAM-Ig was purified from crude culture supernatants by affinity chromatography on Protein A/G Sepharose (Pierce, Rockford, Ill.) according to the manufacturer's instructions and desalted into 50 mM sodium phosphate buffer, pH 7.6, by ultrafiltration on a YM-30 membrane (Amicon, Beverly, Mass.).

Step B Preparation of $^{125}$I-VCAM-Ig

VCAM-Ig was labeled to a specific radioactivity greater that 1000 Ci/mmole with $^{125}$I-Bolton Hunter reagent (New England Nuclear, Boston, Mass.; cat # NEX120-0142) according to the manufacturer's instructions. The labeled protein was separated from unincorporated isotope by means of a calibrated HPLC gel filtration column (G2000SW; 7.5×600 mm; Tosoh, Japan) using uv and radiometric detection.

Step C VCAM-Ig Binding Assay

Compounds of this invention were prepared in DMSO at 100× the desired final assay concentration. Final concentrations were selected from a range between 0.001 nM-100 μM. Jurkat cells were centrifuged at 400×g for five mins and resuspended in binding buffer (25 mM HEPES, 150 mM NaCl, 3 mM KCl, 2 mM glucose, 0.1% bovine serum albumin, pH 7.4). The cells were centrifuged again and resuspended in binding buffer supplemented with MnCl$_2$ at a final concentration of 1 mM. Compounds were assayed in Millipore MHVB multiscreen plates (cat# MHVBN4550, Millipore Corp., Mass.) by making the following additions to duplicate wells: (i) 200 μL of binding buffer containing 1 mM MnCl$_2$; (ii) 20 μL of $^{125}$I-VCAM-Ig in binding buffer containing 1 mM MnCl$_2$ (final assay concentration ~100 pM); (iii) 2.5 μL of compound solution or DMSO; (iv) and 0.5×10$^6$ cells in a volume of 30 mL. The plates were incubated at rt for 30 mins, filtered on a vacuum box, and washed on the same apparatus by the addition of 100 μL of binding buffer containing 1 mM MnCl$_2$. After insertion of the multiscreen plates into adapter plates (Packard, Meriden, Conn., cat# 6005178), 100 μL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Control wells in which cells were omitted were used to determine the level of binding corresponding to 100% inhibition. Binding of $^{125}$I-VCAM-Ig in the absence of cells was usually less than 5% of that observed using cells in the presence of vehicle. Percent inhibition was then calculated for each test well and the $IC_{50}$ was determined from a ten point titration using a validated four parameter fit algorithm.

EXAMPLE 11

Antagonism of $\alpha_4\beta_7$ Dependent Binding to VCAM-Ig Fusion Protein

Step A $\alpha_4\beta_7$ Cell line

RPMI-8866 cells (a human B cell line $\alpha_4{}^+\beta_1{}^-\beta_7{}^+$; a gift from Prof. John Wilkins, University of Manitoba, Canada) were grown in RPMI/10% fetal calf serum/100 U penicillin/ 100 μg streptomycin/2 mM L-glutamine at 37° C., 5% carbon dioxide. The cells were pelleted at 1000 rpm for 5 mins and then washed twice and resuspended in binding buffer (25 mM Hepes, 150 mM NaCl, 0.1% BSA, 3 mM KCl, 2 mM Glucose, pH 7.4).

Step B $\alpha_4\beta_7$ VCAM-Ig Binding Assay

Compounds of this invention were prepared in DMSO at 100× the desired final assay concentration. Final concentrations were selected from a range between 0.001 nM–100 μM. Compounds were assayed in Millipore MHVB multiscreen plates (Cat# MHVBN4550) by making the following sequential additions to duplicate wells: (i) 100 mL/well of binding buffer containing 1.5 mM $MnCl_2$; (ii) 10 mL/well $^{125}$I-VCAM-Ig in binding buffer (final assay concentration <500 pM); (iii) 1.5 mL/well test compound or DMSO alone; (iv) 38 mL/well RPMI-8866 cell suspension ($1.25\times10^6$ cells/well). The plates were incubated at rt for 45 mins on a plate shaker at 200 rpm, filtered on a vacuum box, and washed on the same apparatus by the addition of 100 mL of binding buffer containing 1 mM $MnCl_2$. After insertion of the multiscreen plates into adapter plates (Packard, Meriden, Conn., cat# 6005178), 100 mL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Wells in which cells were omitted were used to determine the level of binding corresponding to 100% inhibition. Percent inhibition was then calculated for each test well and the $IC_{50}$ was determined from a ten point titration using a validated four parameter fit algorithm.

What is claimed is:

1. A compound of Formula I:

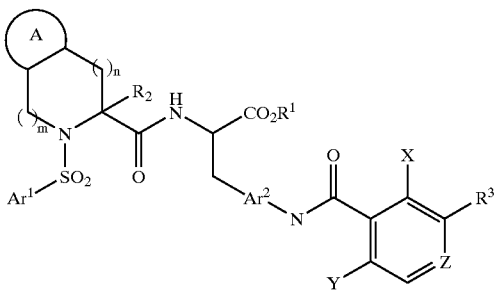

I or a pharmaceutically acceptable salt thereof wherein:
Ring A is an aryl or heteroaryl ring,
  wherein ring A is optionally substituted with one to four substituents independently selected from $R^b$;

X and Y are independently selected from
  1) halogen,
  2) $C_{1-3}$alkyl,
  3) $C_{1-3}$alkoxy;
Z is
  1) N,
  2) $N^+$—$O^-$;
$R^1$ is
  1) hydrogen,
  2) $C_{1-10}$alkyl,
  3) aryl-$C_{1-10}$alkyl;
$R^2$ is
  1) hydrogen or
  2) $C_{1-10}$alkyl,
wherein alkyl is optionally substituted with one to four substituents selected from a group independently selected from $R^c$;
$R^3$ is
  1) hydrogen;
  2) OH;
  3) $OCH_3$; or
  4) $NH_2$;
$R^a$ is
  1) —$OR^d$,
  2) —$NR^dS(O)_mR^e$,
  3) —$NO_2$,
  4) halogen
  5) —$S(O)_pR^d$,
  6) —$SR^d$,
  7) —$S(O)_2OR^d$,
  8) —$S(O)_mNR^dR^e$,
  9) —$NR^dR^e$,
  10) —$O(CR^fR^g)_nNR^dR^e$,
  11) —$C(O)R^d$,
  12) —$CO_2R^d$,
  13) —$CO_2(CR^fR^g)_nCONR^dR^e$,
  14) —$OC(O)R^d$,
  15) —CN,
  16) —$C(O)NR^dR^e$,
  17) —$NR^dC(O)R^e$,
  18) —$OC(O)NR^dR^e$,
  19) —$NR^dC(O)OR^e$,
  20) —$NR^dC(O)NR^dR^e$,
  21) —$CR^d(N$—$OR^e)$,
  22) $CF_3$,
  23) —$OCF_3$,
  24) $C_{3-8}$cycloalkyl, or
  25) heterocyclyl;
wherein cycloalkyl and heterocyclyl are optionally substituted with one to four groups independently selected from $R^c$;
$R^b$ is
  1) a group selected from $R^a$,
  2) $C_{1-10}$ alkyl,
  3) $C_{2-10}$ alkenyl,
  4) $C_{2-10}$ alkynyl,
  5) $Ar^1$,
  6) $C_{1-10}$alkyl-$Ar^1$,
wherein alkyl, alkenyl, alkynyl, and $Ar^1$ are optionally substituted with one to four substituents selected from a group independently selected from $R^c$;
$R^c$ is
  1) halogen,
  2) amino,
  3) carboxy,
  4) $C_{1-4}$alkyl, 5) $C_{1-4}$alkoxy,
6) aryl,
7) aryl $C_{1-4}$alkyl,
8) hydroxy,
9) cyano,
10) $CF_3$,
11) $OCF_3$
12) $OC(O)C_{1-4}$alkyl,
13) $OC(O)NR^fR^g$, or
14) aryloxy;

$R^d$ and $R^e$ are independently selected from hydrogen, $C_{1-10}$alkyl, $C_{2-10}$alkenyl, $C_{2-10}$alkynyl, Cy and Cy $C_{1-10}$alkyl, wherein alkyl, alkenyl, alkynyl and Cy are optionally substituted with one to four substituents independently selected from Re; or $R^d$ and $R^g$ together with the atom(s) to which they are attached form a heterocyclic ring of 4 to 7 members containing 0–2 additional heteroatoms independently selected from oxygen, sulfur and N-Rh;

$R^f$ and $R^g$ are independently selected from hydrogen, $C_{1-10}$alkyl, Cy and Cy-$C_{1-10}$alkyl; or $R_f$ and $R_g$ together with the carbon to which they are attached form a ring of 5 to 7 members containing 0–2 heteroatoms independently selected from oxygen, sulfur and nitrogen;

$R^h$ is selected from $R^f$ and —$C(O)R^f$;

Cy is selected from cycloalkyl, heterocyclyl, aryl, and heteroaryl;

$Ar^1$ is selected from phenyl, pyridyl, pyridazinyl, pyrimidinyl, pyrazinyl and triazinyl each optionally substituted with one or two groups independently selected from $R^c$;

$Ar^2$ is 1,4-phenylene or 2,5-pyridylene;

p is 1 or 2;

m is 0, 1 or 2;

n is 0, 1 or 2.

2. A compound of claim 1 wherein $Ar^1$ is 3-substituted phenyl optionally having a second substituent on the 5-position wherein the substituents are independently selected from chloro, fluoro, bromo, methyl, trifluoromethyl and trifluoromethoxy.

3. A compound of claim 1 wherein $Ar^2$ is 1,4-phenylene.

4. A compound of claim 1 wherein X or Y is chloro and the other is either chloro or methoxy.

5. A compound of claim 1 having the formula Ia:

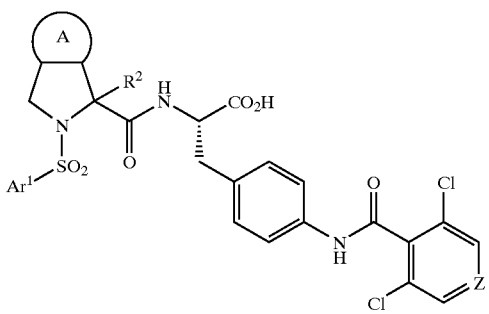

Ia wherein Z is N or
Ring A is phenyl, or pyrazolyl;
$R^2$ is H or methyl;
$Ar^1$ is phenyl optionally substituted with 1 or 2 meta-substituents wherein said substituents are independently selected from hydrogen, halogen, cyano, or carboxyl; or a pharmaceutically acceptable salt thereof.

6. A method for inhibiting cell adhesion in a mammal which comprises administering to said mammal an effective amount of a compound of claim 1.

7. A method for the treatment of diseases, disorders, conditions or symptoms mediated by cell adhesion in a mammal which comprises administering to said mammal an effective amount of a compound of claim 1.

8. A method for the treatment of asthma in a mammal which comprises administering to said mammal a therapeutically effective amount of a compound of claim 1.

9. A method for the treatment of allergic rhinitis in a mammal which comprises administering to said mammal a therapeutically effective amount of a compound of claim 1.

10. A method for the treatment of multiple sclerosis in a mammal which comprises administering to said mammal a therapeutically effective amount of a compound of claim 1.

11. A method for the treatment of inflammation in a mammal which comprises administering to said mammal an effective amount of a compound of claim 1.

12. A method for the treatment of inflammatory bowel disease in a mammal which comprises administering to said mammal a therapeutically effective amount of a compound of claim 1.

13. A pharmaceutical composition which comprises a compound of claim 1 and a pharmaceutically acceptable carrier thereof.

14. A compound of claim 4 wherein X and Y are each chloro.

* * * * *

UNITED STATES PATENT AND TRADEMARK OFFICE
CERTIFICATE OF CORRECTION

PATENT NO. : 6,559,174 B2
DATED : May 6, 2003
INVENTOR(S) : Linus S. Lin et al.

It is certified that error appears in the above-identified patent and that said Letters Patent is hereby corrected as shown below:

<u>Column 31,</u>
Lines 18 and 19, should read:
-- selected from $R^c$; or
 $R^d$ and $R^e$ together with the atom(s) to which they are --.

<u>Column 32,</u>
Line 17, should read:
-- wherein Z is N or $N^+O^-$; --

Signed and Sealed this

Twenty-fifth Day of November, 2003

JAMES E. ROGAN
*Director of the United States Patent and Trademark Office*